US012768764B2

(12) United States Patent
Sakurai et al.

(10) Patent No.: US 12,768,764 B2
(45) Date of Patent: Oct. 20, 2026

(54) ABNORMALITY DETERMINATION DEVICE, CONDUCTIVE PARTICLE DETECTING DEVICE, AND ABNORMALITY DETERMINATION METHOD

(71) Applicant: Nabtesco Corporation, Tokyo (JP)

(72) Inventors: Kazuhiko Sakurai, Tokyo (JP); Masaki Harada, Tokyo (JP)

(73) Assignee: NABTESCO CORPORATION, Tokyo (JP)

( * ) Notice: Subject to any disclaimer, the term of this patent is extended or adjusted under 35 U.S.C. 154(b) by 276 days.

(21) Appl. No.: 18/686,217

(22) PCT Filed: Jul. 20, 2022

(86) PCT No.: PCT/JP2022/028197
§ 371 (c)(1),
(2) Date: Feb. 23, 2024

(87) PCT Pub. No.: WO2023/053683
PCT Pub. Date: Apr. 6, 2023

(65) Prior Publication Data

US 2024/0353303 A1 Oct. 24, 2024

(30) Foreign Application Priority Data

Sep. 28, 2021 (JP) ................................ 2021-157903

(51) Int. Cl.
*G01N 15/06* (2024.01)
*G01N 27/04* (2006.01)
*G01N 33/28* (2006.01)

(52) U.S. Cl.
CPC ..... *G01N 15/0656* (2013.01); *G01N 33/2858* (2013.01); *G01N 33/2888* (2013.01)

(58) Field of Classification Search
CPC .... G01N 15/00; G01N 15/06; G01N 15/0656; G01N 27/00; G01N 27/04-10; G01N 33/28; G01N 33/2858; G01N 33/2888
See application file for complete search history.

(56) References Cited

U.S. PATENT DOCUMENTS 4,008,464 A * 2/1977 Hobbie .................. F16N 29/04 210/85
4,070,660 A 1/1978 Tauber
(Continued)

FOREIGN PATENT DOCUMENTS

JP 03-123926 U 12/1991
JP 2005-331324 A 12/2005
(Continued)

OTHER PUBLICATIONS

Extended European Search Report dated Sep. 8, 2025, issued in corresponding to European Patent Application No. 22875561.7 (9 pgs.).

(Continued)

*Primary Examiner* — Nguyen Q. Ha
(74) *Attorney, Agent, or Firm* — Pillsbury Winthrop Shaw Pittman, LLP

(57) ABSTRACT

An abnormality determination device of the disclosure includes: an acquisition unit (601) acquiring an electrical resistance value between electrodes in a non-conductive lubricant used for lubrication of a mechanical device, the electrodes being spaced apart from each other in the lubricant; an abnormality determining unit (602) determining whether there is an abnormality in the mechanical device based on a number of times the resistance value acquired by the acquisition unit falls below a threshold; and an output unit (603) outputting a result of the determination by the abnormality determining unit. The acquiring unit acquires
(Continued)

the electrical resistance between the electrodes that varies depending on conductive particles collected by magnetic force in the lubricant.

8 Claims, 9 Drawing Sheets

(56) References Cited

U.S. PATENT DOCUMENTS

| | | | | |
|---|---|---|---|---|
| 4,686,857 A * | 8/1987 | Kato | G01N 33/2888 | 73/304 C |
| 4,731,578 A * | 3/1988 | Tsaprazis | G01N 33/2858 | 324/225 |
| 5,179,346 A * | 1/1993 | McGee | G01N 15/0656 | 324/693 |
| 5,264,832 A * | 11/1993 | Parmer | G01N 15/0656 | 73/61.42 |
| 7,106,075 B2 * | 9/2006 | Hu | G01N 15/0266 | 324/698 |
| 10,705,038 B2 * | 7/2020 | Ricci | G01N 33/22 | |
| 2008/0143351 A1 | 6/2008 | Lee et al. | | |
| 2012/0046896 A1 * | 2/2012 | Flandrois | G01N 27/10 | 702/65 |
| 2014/0347032 A1 * | 11/2014 | Reed | G01N 33/2858 | 324/71.1 |
| 2018/0030850 A1 * | 2/2018 | Hagen | F16N 29/04 | |
| 2018/0187622 A1 * | 7/2018 | Rudolecky | F01M 11/10 | |
| 2019/0162687 A1 | 5/2019 | Best | | |
| 2020/0340936 A1 | 10/2020 | Sakurai et al. | | |
| 2023/0054919 A1 * | 2/2023 | Al-Khairy | G01N 15/0606 | |

FOREIGN PATENT DOCUMENTS

| | | |
|---|---|---|
| JP | 2007-003435 A | 1/2007 |
| JP | 2020-183932 A | 11/2020 |
| JP | 2021-096168 A | 6/2021 |

OTHER PUBLICATIONS

Notice of Allowance dated Nov. 5, 2024, issued in corresponding Japanese Patent Application No. 2023-550405 with English translation (6 pgs.).

International Search Report issued in corresponding International Application No. PCT/JP2022/028197, dated Oct. 4, 2022.

* cited by examiner

ABNORMALITY DETERMINATION DEVICE, CONDUCTIVE PARTICLE DETECTING DEVICE, AND ABNORMALITY DETERMINATION METHOD

CROSS-REFERENCE TO RELATED APPLICATIONS

This application is the U.S. National Phase of PCT/JP2022/028197, filed Jul. 20, 2022, which in turn claims priority to Japanese Patent Application No. 2021-157903 filed Sep. 28, 2021. The content of these applications are incorporated herein by reference in their entireties.

TECHNICAL FIELD

The present disclosure relates to an abnormality determination device, a conductive particle detecting device, an abnormality determination method, and a program. This application is based on and claims the benefit of priority from Japanese Patent Application Serial No. 2021-157903 (filed on Sep. 28, 2021), the contents of which are hereby incorporated by reference in their entirety.

BACKGROUND

Mechanical devices include a built-in mechanical mechanism such as a speed reducer. In such a mechanical device, a casing is filled with a lubricant to reduce wear of the mechanical mechanism. Abrasion and damage may occur in mechanical parts of the mechanical device used over time. Metal powder produced from the mechanical parts due to abrasion and damage may mix into the lubricant. When a large amount of metal powder mixes into the lubricant, the function of the lubricant (the ability to inhibit the abrasion in the mechanism) is decreased. The presence of the large amount of metal powder mixed into the lubricant indicates that the abrasion or damage has occurred in the mechanism.

Therefore, for the mechanical devices, it is desirable to externally detect that the amount of the metal powder mixed into the lubricant has exceeded a preset value. To address this, devices in which the metal powder in the lubricant are attracted by a permanent magnet and thereby electrically detecting the amount of the attracted metal powder have been known (see, for example, Patent Literature 1).

RELEVANT REFERENCE

List of Relevant Patent Literature

Patent Literature 1: Japanese Patent Application Publication No. 2005-331324

SUMMARY

However, from the perspective of a user of the mechanical device, it was sometimes impossible to use the mechanical device in a planned manner because a failure of the mechanical device is suddenly informed without any prior warning. This is inconvenient for the user of the mechanical device.

The present disclosure provides an abnormality determination device, a conductive particle detecting device, an abnormality determination method, and a program that can improve the convenience of users who use mechanical devices.

(1) An abnormality determination device according to one aspect of the disclosure includes: an acquisition unit acquiring an electrical resistance value between electrodes in lubricant used for lubrication of a mechanical device, the electrodes being spaced apart from each other in the lubricant; an abnormality determining unit determining whether there is an abnormality in the mechanical device based on a number of times the resistance value acquired by the acquisition unit falls below a threshold; and an output unit outputting a result of the determination by the abnormality determining unit. The acquiring unit acquires the electrical resistance between the electrodes that varies depending on conductive particles collected by magnetic force in the lubricant.

(2) In the above abnormality determination device, the acquisition unit may acquire electrical resistance values between two or more pairs of electrodes in different combinations. The abnormality determining unit may determine the abnormality based on the number of times the electrical resistance values have fallen below the threshold.

(3) In the above abnormality determination device, The abnormality determining unit may determine the abnormality based on a sum of the number of times each of the electrical resistance values has fallen below the threshold.

(4) In the above abnormality determination device, the abnormality determining unit may determine the abnormality including a failure state indicating a failure of the mechanical device and a warning state before the failure state. The output unit may output information indicating either the failure state or the warning state.

(5) In the above abnormality determination device, the threshold may be a value that can be changed depending on a size of the mechanical device.

(6) In the above abnormality determination device, the threshold may be a value that can be changed depending on at least one of viscosity or insulation properties of the lubricant.

(7) In the above abnormality determination device, the number of times may be a value that can be changed depending on a size of the mechanical device.

(8) An abnormality determination device according to another aspect of the disclosure includes: an acquisition unit acquiring an electrical resistance value between electrodes in a non-conductive lubricant used for lubrication of a mechanical device, the electrodes being spaced apart from each other in the lubricant; an abnormality determining unit determining whether there is an abnormality in the mechanical device based on a number of times the resistance value acquired by the acquisition unit falls below a threshold; and an output unit outputting a result of the determination by the abnormality determining unit, wherein the acquiring unit acquires the electrical resistance between the electrodes that varies depending on conductive particles collected by magnetic force in the lubricant, the acquisition unit further acquires electrical resistance values between two or more pairs of electrodes in different combinations, and the abnormality determining unit determines the abnormality including the failure state indicating a failure of the mechanical device and the warning state before the failure state based on a sum of the number of times each of the electrical resistance values has fallen below the threshold, and wherein the output unit outputs information indicating either the failure state or the warning state.

(9) A conductive particle detecting device according to yet another aspect of the disclosure includes: electrodes in a non-conductive lubricant used for lubrication of a mechanical device, the electrodes being spaced apart from each other in the lubricant; an acquiring unit acquiring an electrical resistance between the electrodes that varies depending on conductive particles collected by magnetic force in the lubricant; an abnormality determining unit determining whether there is an abnormality in the mechanical device based on a number of times the resistance value acquired by the acquisition unit falls below a threshold; and an output unit outputting a result of the determination by the abnormality determining unit,

(10) An abnormality determination method performed by a computer used for an abnormality determination device to function as: acquiring an electrical resistance value between electrodes in a non-conductive lubricant used for lubrication of a mechanical device, the electrodes being spaced apart from each other in the lubricant; determining whether there is an abnormality in the mechanical device based on a number of times the resistance value acquired by the acquisition unit falls below a threshold; and outputting a result of the determination made in the determining. The acquiring includes acquiring the electrical resistance between the electrodes that varies depending on conductive particles collected by magnetic force in the lubricant.

(11) A program causing a computer used for an abnormality determination device to function as: an acquisition unit acquiring an electrical resistance value between electrodes in a non-conductive lubricant used for lubrication of a mechanical device, the electrodes being spaced apart from each other in the lubricant; an abnormality determining unit determining whether there is an abnormality in the mechanical device based on a number of times the resistance value acquired by the acquisition unit falls below a threshold; and an output unit outputting a result of the determination by the abnormality determining unit. The acquiring unit acquires the electrical resistance between the electrodes that varies depending on conductive particles collected by magnetic force in the lubricant.

Advantageous Effects

With the above described abnormality determination device, conductive particle detecting device, abnormality determination method, and program, it is possible to improve the user's convenience in using mechanical devices.

DESCRIPTION OF THE EMBODIMENTS

Embodiment

The following describes embodiments of the present disclosure with reference to the drawings.

Example of Speed Reducer Relating to Embodiment

Figure 1:
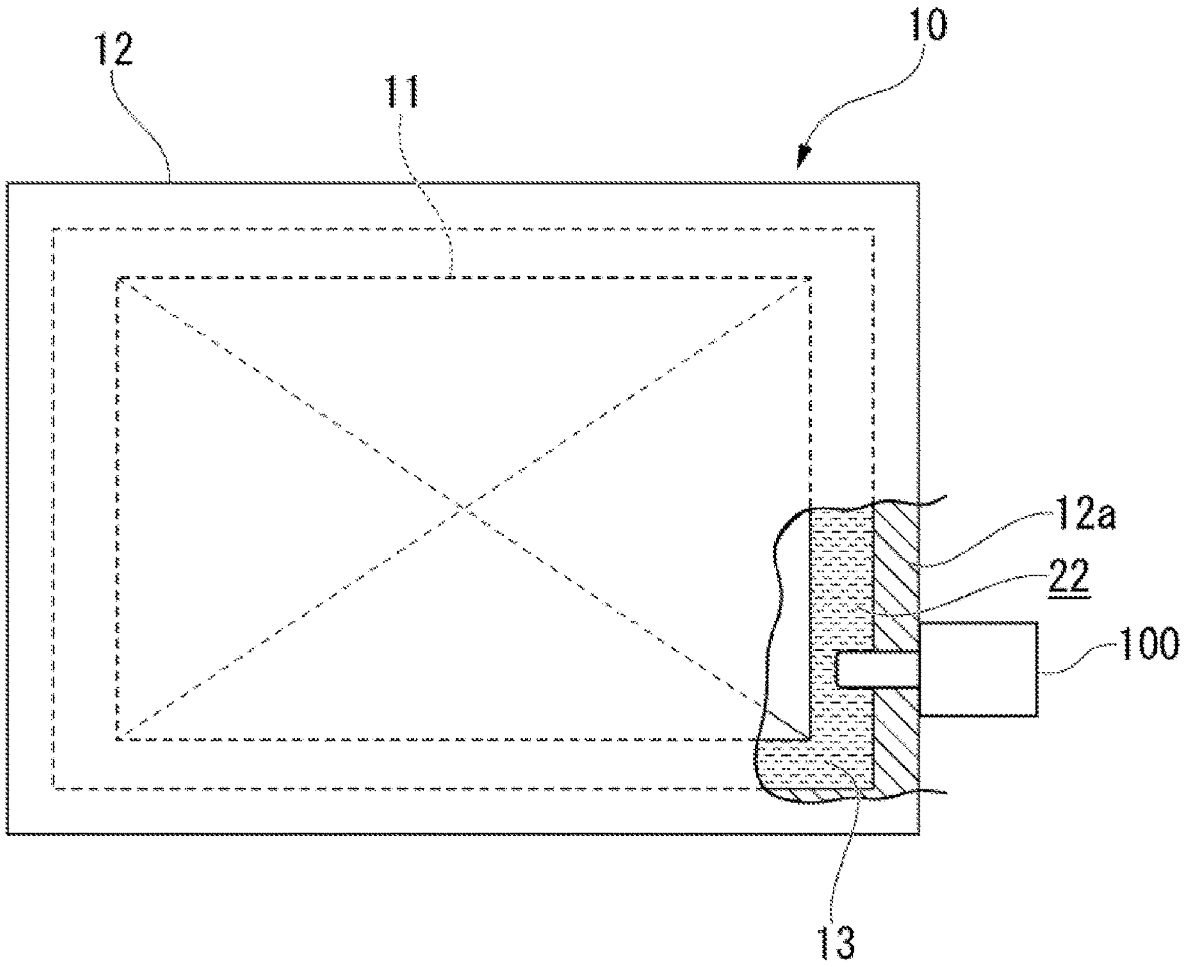
FIG. 1 illustrates an example of a speed reducer 10 relating to an embodiment of the present disclosure.

FIG. 1 illustrates an example of the speed reducer 10 relating to the embodiment. The speed reducer 10 shown in FIG. 1 is an example of a mechanical device. The speed reducer 10 is used in, for example, the joints of industrial robots used in the production lines of plants.

The speed reducer 10 includes a speed reduction mechanism 11 and a casing 12. The speed reduction mechanism 11 reduces the speed of the rotation at a predetermined reduction ratio. The casing 12 houses the speed reduction mechanism 11 thereinside. An oil bath 22 is provided inside the casing 12. The oil bath 22 is filled with lubricant 13 to lubricate the speed reduction mechanism 11 and other machine contact parts. A non-conductive lubricant is used as the lubricant 13.

A conductive particle detecting device 100 is provided on a wall 12*a* of the casing 12. The conductive particle detecting device 100 is disposed at a site where the lubricating fluid 13 is highly flowable. The conductive particle detecting device 100 detects conductive particles such as metal powder mixing into the lubricant 13.

<Configuration of Conductive Particle Detecting Device>

Figure 2:
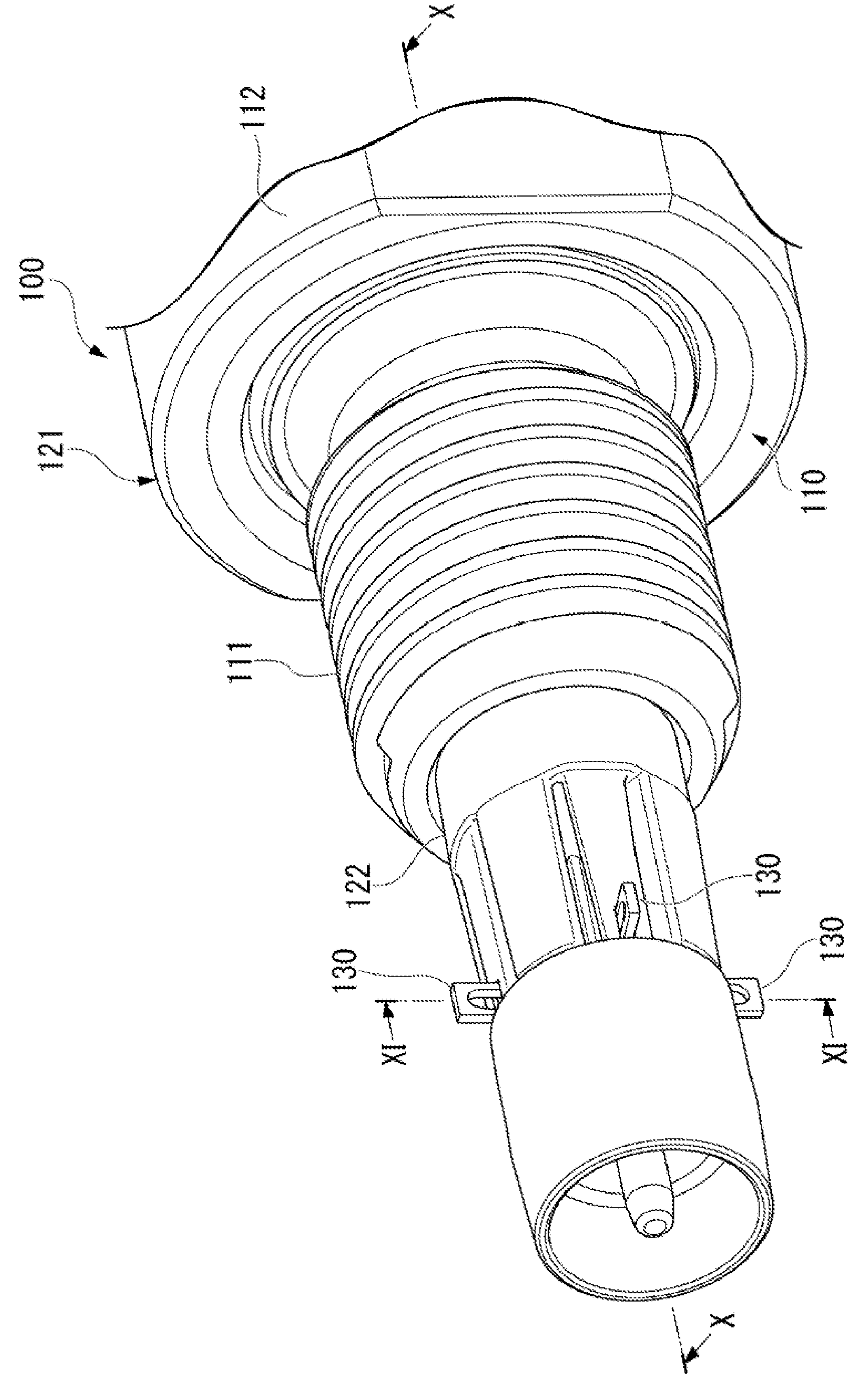
FIG. 2 is a perspective view of an example of a conductive particle detecting device 100.
Figure 3:
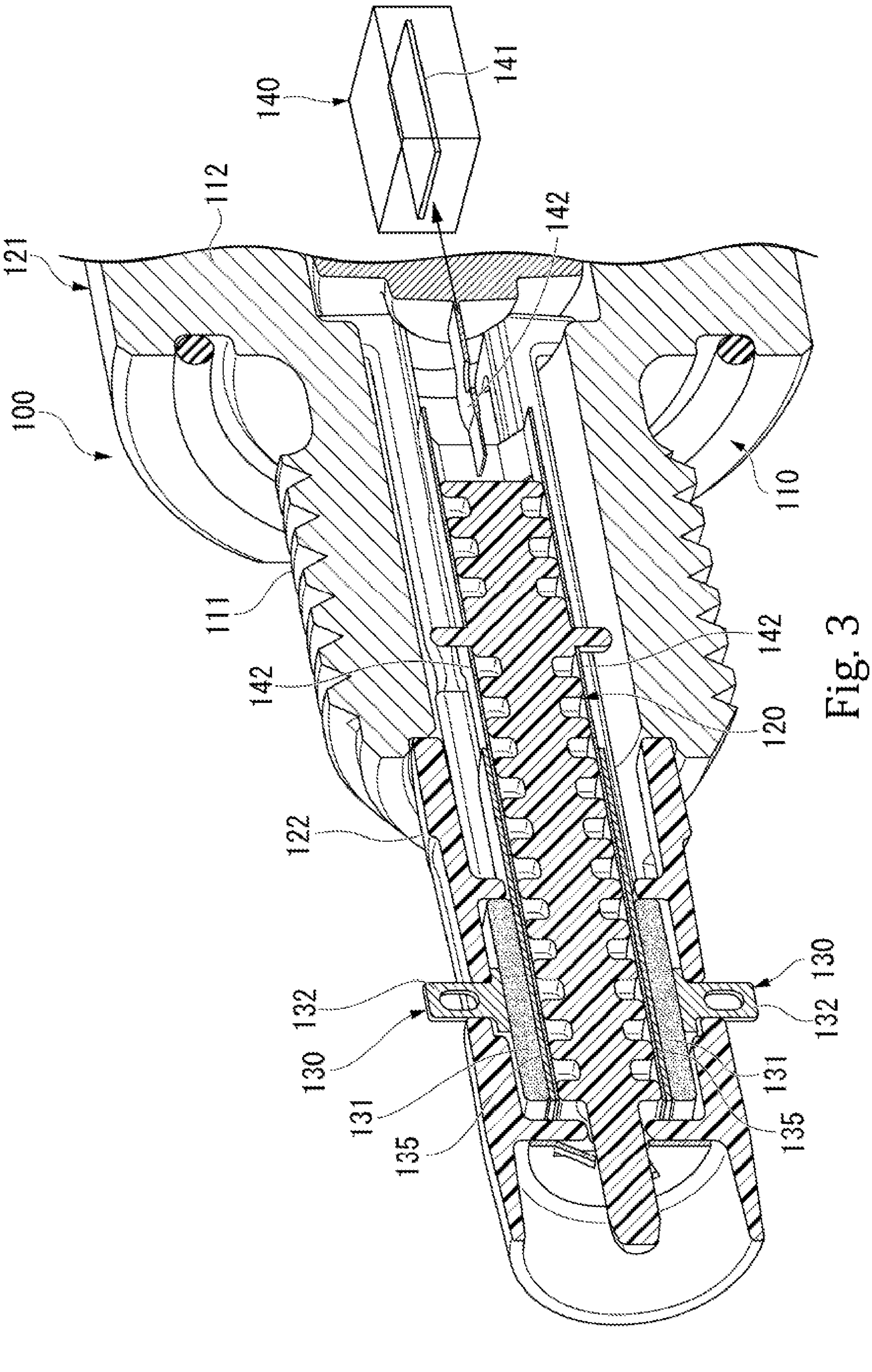
FIG. 3 is a partial sectional perspective view of the conductive particle detecting device 100 of FIG. 2 cut along the line X-X.

FIG. 2 is a perspective view of an example of the conductive particle detecting device 100. FIG. 3 is a partial sectional perspective view showing the conductive particle detecting device 100 of FIG. 2 cut along the line X-X. As shown in FIGS. 2 and 3, the conductive particle detecting device 100 includes an attachment unit 110, a support member 120 (see FIG. 3), four electrodes 130, and the control device 140 (see FIG. 3).

The attachment unit 110 includes a threaded portion 111 and a flange 112. The threaded portion 111 is installed in a thread hole that penetrates the wall 12*a*. The flange 112 is a flange nut for tightening the threaded portion 111 to the wall 12*a*. The flange 112 is formed integrally with the threaded portion 111 at the end of the threaded portion 111.

The support member 120 is formed of a resin material. The threaded portion 111 penetrates the support member 120 in the axial direction. One end of the support member 120 is fixed to the inner side of a device body 121 in the longitudinal direction. The other end of the support member 120 in the longitudinal direction protrudes outwardly from the threaded portion 111.

The four electrodes 130 each have a permanent magnet 131 and a projection member 132. The permanent magnet 131 is a conductive magnet. The permanent magnet 131 has the properties of a magnet without receiving an external magnetic field or current supply. The permanent magnet 131 attracts and fixes a relay piece 135 made of a metal magnetic material by magnetic force.

The projection member 132 protrudes outward from a detection unit cover 122. The projection member 132 is attached to the permanent magnet 131. The projection member 132 is formed of a conductive non-magnetic material such as brass, aluminum, or copper. The projection member 132 is provided in contact with the permanent magnet 131. However, the projection member 132 does not directly attract metal powder.

The control device 140 is an example of an abnormality determination device. The control device 140 is disposed inside a device cover 101 (see FIG. 4). The control device 140 is equipped with a detecting circuit board 141. The detecting circuit board 141 is connected to a flexible printed wiring board 142. The flexible printed wiring board 142 includes conductive portions. One end of the flexible printed wiring board 142 is connected to the detecting circuit board 141, and the other end is branched in four directions. Each of the four branched ends is connected to corresponding one of the relay pieces 135 via a terminal (conductive portion). Specifically, the terminal (conductive portion) of each end portion is located between the support member 120 and the relay piece 135. The terminals are connected to the relay pieces 135 by conductive adhesive, soldering, or other means.

<Detecting Circuit for Metal Powder>

Figure 4:
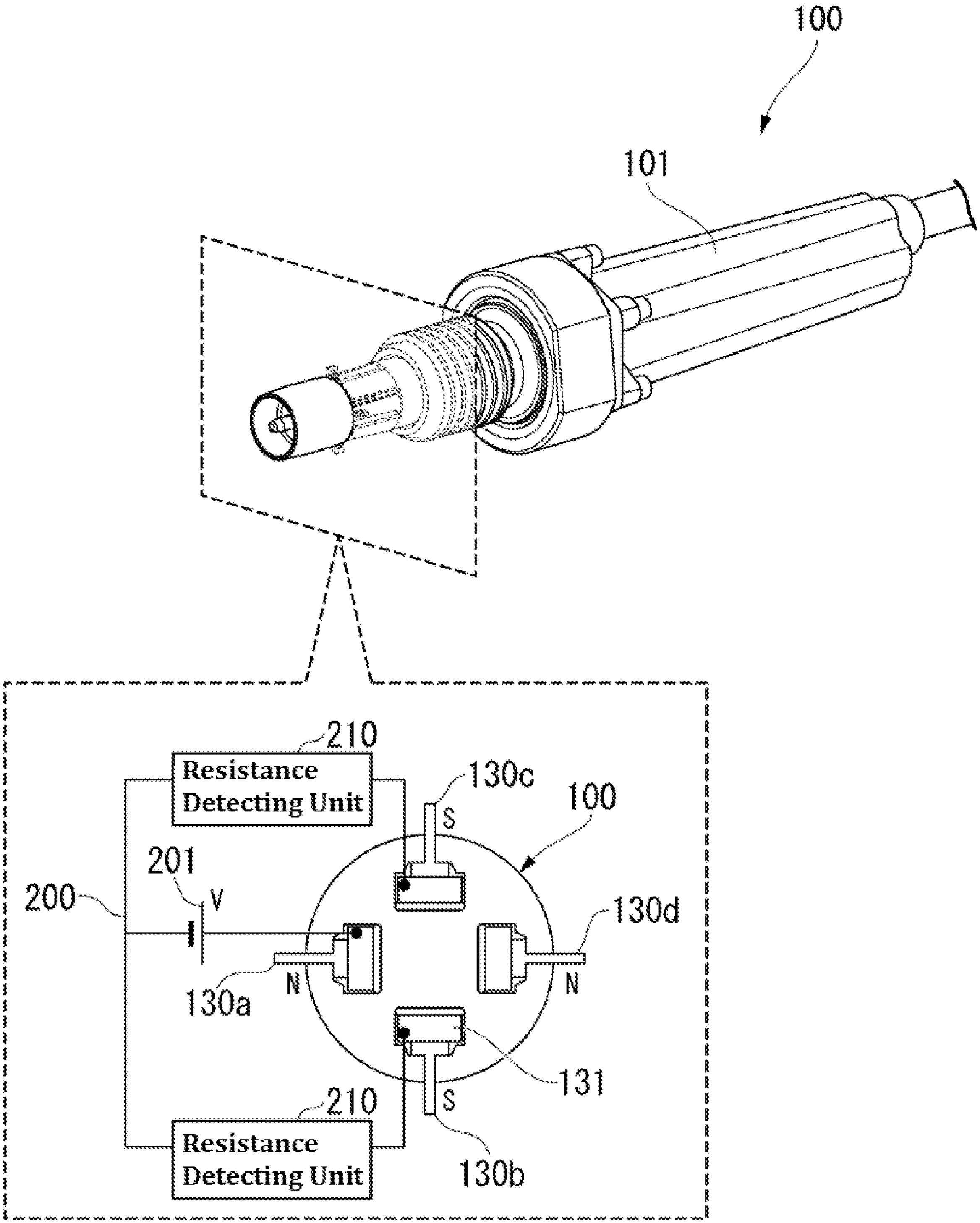
FIG. 4 illustrates a detecting circuit through a section of the conductive particle detecting device 100 of FIG. 2 along the XI-XI line.

FIG. 4 illustrates a detecting circuit through a section of the conductive particle detecting device 100 of FIG. 2 along the XI-XI line. A detecting circuit 200 shown in FIG. 4 is provided on the detecting circuit board 141. The detecting circuit 200 is a circuit in which a first electrode 130*a* and second electrodes 130*b* and 130*c* are connected via a power supply 201. A higher voltage is applied to the first electrode 130*a* than to the second electrodes 130*b* and 130*c*. The magnetic polarity of the first electrode 130*a* is, for example, north pole. The magnetic polarity of the second electrodes 130*b* and 130*c* are, for example, south pole.

The detecting circuit 200 is equipped with a resistance detecting unit 210. The resistance detecting unit 210 detects the electrical resistance (hereinafter referred to as "resistance") between the two adjacent electrodes 130 (between first electrode 130*a* and second electrode 130*b*, and between first electrode 130*a* and second electrode 130*c*).

<Initial Metal Powder and Long-Use Metal Powder>

Initial metal powder produced when the speed reducer 10 is first used is fine metal powder having a particle size of less than 10 μm (normally less than 2 μm). The initial metal powder is generated in the initial phase of use. In the initial phase of use, the initial metal powder flows in the oil bath 22 with the lubricant 13 and a small amount of the initial metal powder may adhere to a surface of the detection unit cover 122 as a lower layer. The lubricant 30 remains as a non-conductive layer around the initial metal powder adhering to the detection unit cover 122. During the initial phase of the use of the speed reducer, the resistance detecting unit 210 detects an infinite resistance since the lubricant 13 is non-conductive. Since the attracting force of the initial metal powder is relatively weak, the amount of the initial metal powder collected between the first electrode 130*a* and the second electrode 130*b* (or the second electrode 120*c*) is also small.

On the other hand, metal (wear powder) and metal powder such as broken pieces (long-use metal powder particles) are generated by normal use of the speed reducer 10. The long-use metal powder particles have a large particle size, for example, 10 μm or more. Therefore, the long-use metal powder particles receive a large attractive force from the permanent magnets 131. Since the long-use metal powder particles are subjected to a large attracting force, they push aside the non-conductive lubricant and come into contact with each other. When a large amount of the long-use metal powder particles mix into the lubricant 13, the long-use metal powder particles in the lubricant 13 are attracted by the plurality of permanent magnets 131 of the conductive particle detecting device 100. The long-use metal powder particles then adhere to the gap between the electrodes 130 on the outer surface of the detection unit cover 122. Since the long-use metal powder particles receive a large attracting force from the permanent magnet 131, they are securely attracted even from the upper side of the initial metal powder. Therefore, the long-use metal powder particles are inevitably deposited as an upper layer on top of the initial metal powder.

When the amount of the long-use metal powder particles adhering to the outer surface of the detection unit cover 122 increases beyond a certain amount, the resistance value between the adjacent permanent magnets 131 (resistance value detected by the resistance detecting unit 210) decreases below a specified value. In this way, it is possible for the control device 140 to inform an external user terminal or the like that the amount of the long-use metal powder in the speed reducer 10 has increased.

<Failure of Speed Reducer>

Figure 5A:
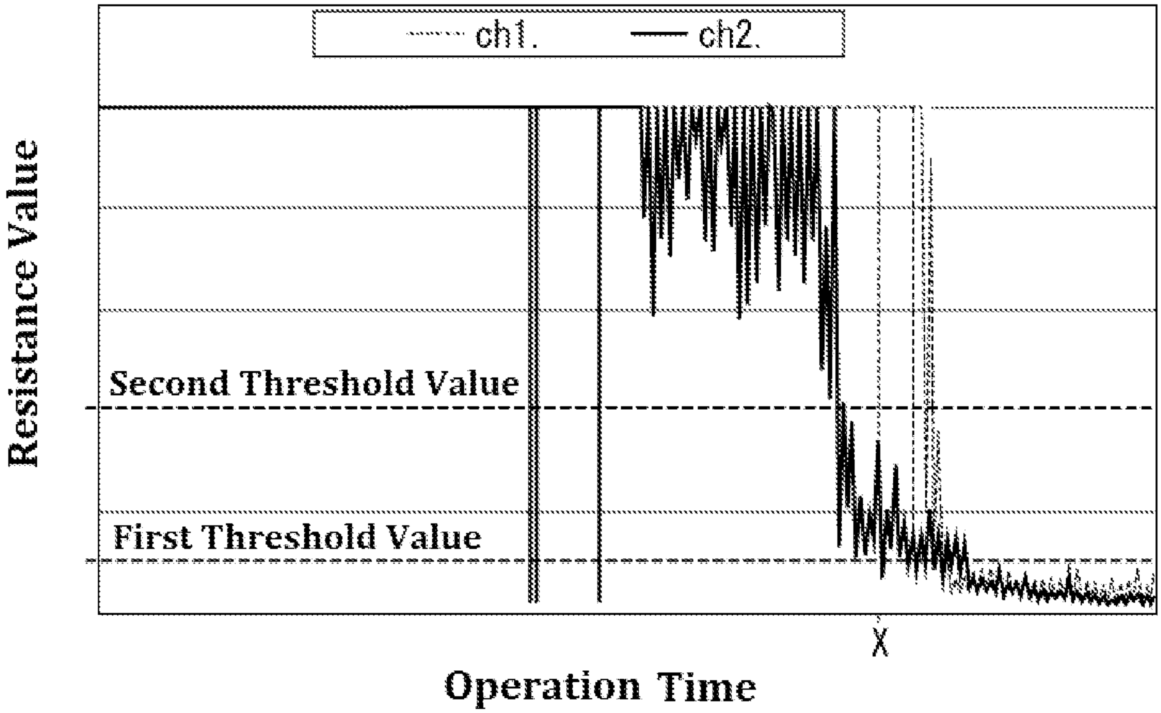
FIG. 5A is a graph showing an example of resistance values detected by a resistance detecting unit 210.
Figure 5B:
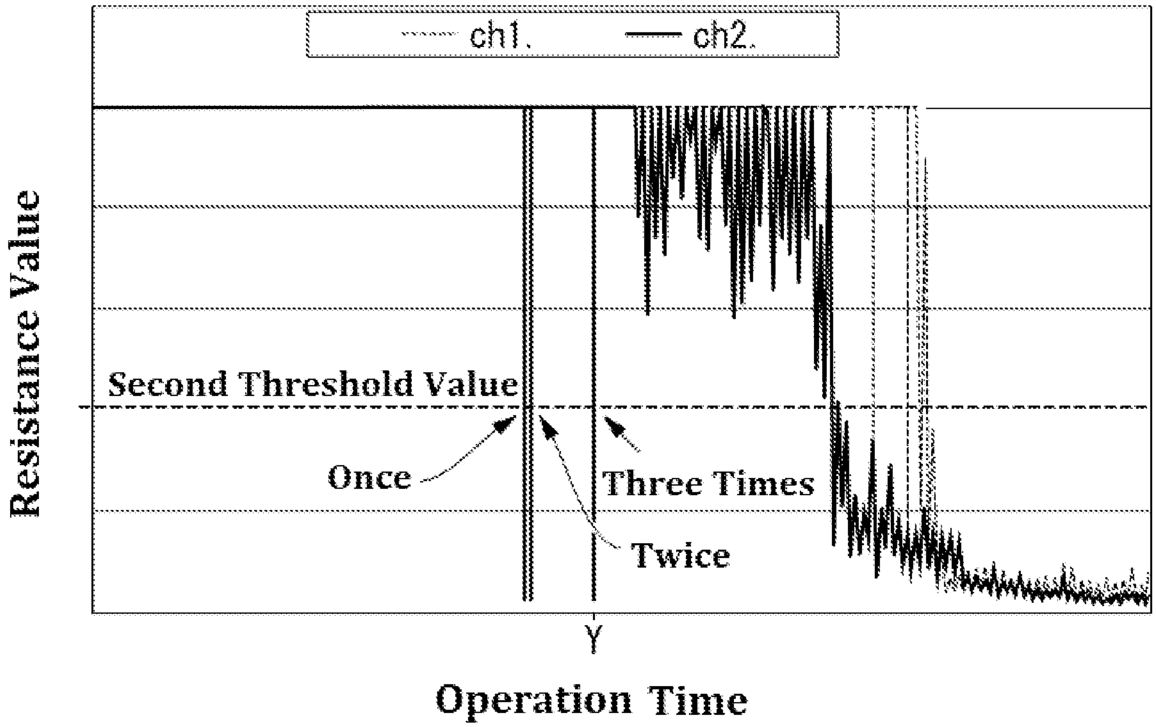
FIG. 5B is another graph showing an example of resistance values detected by the resistance detecting unit 210.

FIGS. 5A and 5B are graphs showing examples of resistance values detected by the resistance detecting unit 210. In FIGS. 5A and 5B, the horizontal axis indicates the operation time (rated conversion time) of the speed reducer 10, and the vertical axis indicates the resistance value detected by the resistance detecting unit 210. Channel 1 (ch1) shows, for example, the resistance between the first electrode 130*a* and the second electrode 130*b*. Channel 2 (ch2) shows, for example, the resistance value between the first electrode 130*a* and the second electrode 130*c*. The waveforms of each channel shown in FIGS. 5A and 5B have the same wave pattern.

For example, as shown in FIG. 5A, assume that the reducer 10 has failed when the resistance values of both channel 1 and channel 2 fall below a threshold value at the same time. In this case, for example, assuming that the resistance threshold is a first threshold, the resistance values of both channels 1 and 2 simultaneously fall below the first threshold at time X. Whereas assuming that the resistance threshold value is a second threshold value, which is higher than the first threshold value, the resistance values of both channels 1 and 2 simultaneously fall below the second threshold value at the same time X. In other words, changing the threshold value does not change the time to detect a failure. Therefore, simply changing the threshold value for the resistance value is not enough to detect a failure of the reducer 10 with high accuracy.

Even when the long-use metal powder particles adhere to the conductive particle detecting device 100, the speed reducer 10 does not immediately fail. Specifically, as shown in the waveforms of channel 2 of FIGS. 5A and 5B, the resistance value does not immediately drop to 0Ω when the long-use metal powder particles adhere to the device. The resistance value tends to decrease and increase several times, and may eventually converge to several tens of kΩ. This means, for example, that although the long-use metal powder particles once adhered to the outer surface of the detection unit cover 122, the flow of the lubricant 13 may peel off the adhered metal powder particles. However, the fact that the conductive particle detecting device 100 has detected the adhesion of the long-use metal powder particles means that the long-use metal powder particles are present in the oil bath 22.

Therefore, as shown in FIG. 5B, the embodiment is configured to measure the number of times the resistance value falls below the second threshold value and detect an abnormality in the speed reducer 10 when the number reaches a prescribed number of times (e.g., three times). This allows the abnormality to be detected at an early stage (time Y in the figure: Y<X) even if the threshold value is set higher (the second threshold value).

<Functional Configuration of Controller>

Figure 6:
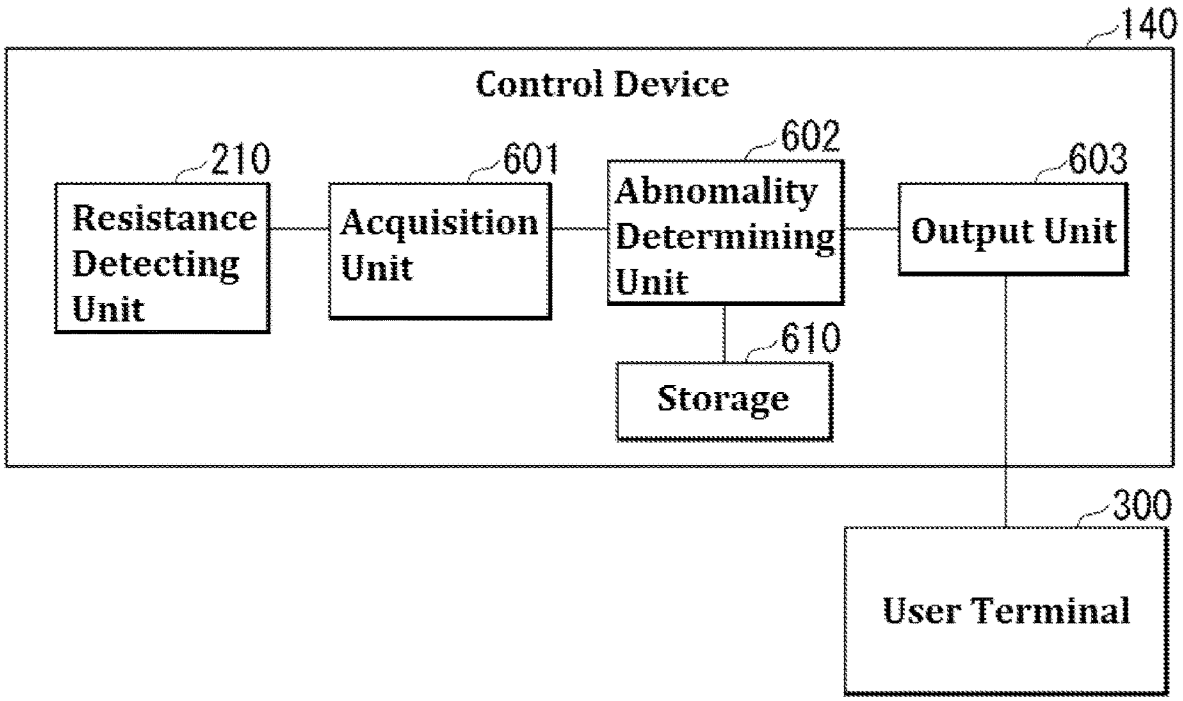
FIG. 6 is a functional block diagram showing an example of functional configuration of a control device 140.

FIG. 6 is a functional block diagram showing an example of functional configuration of the control device 140. As shown in FIG. 6, the control device 140 includes the resistance detecting unit 210, an acquisition unit 601, an abnormality determining unit 602, an output unit 603, and a storage 610. The resistance detecting unit 210 may be provided in a different part (such as on another board) from the control device 140.

The resistance detecting unit 210, acquisition unit 601, abnormality determining unit 602, and output unit 603 may be realized by a hardware processor such as a CPU (Central Processing Unit) executing an abnormality determination program. Some or all of the resistance detecting unit 210, acquisition unit 601, abnormality determining unit 602, and output unit 603 may be implemented by using hardware (including circuitry) such as an LSI (large scale integrated circuit), an ASIC (application specific integrated circuit), an FPGA (field-programmable gate array), and a GPU (graphics processing unit) or may be implemented by the combination of software and hardware.

The abnormality determination program may be stored in advance in a storage device such as a hard disk drive (HDD) or flash memory (storage device with non-transitory storage medium). Alternatively, the abnormality determination program may be stored in a removable storage medium (non-transitory storage medium) such as a DVD or CD-ROM and installed when the storage medium is attached to the drive device. The processor executes the abnormality determination program stored in the storage 610 to implement the functions of the resistance detecting unit 210, the acquisition unit 601, the abnormality determining unit 602, and the output unit 603. The storage 610 includes, for example, volatile memory such as RAM (Random Access Memory) and nonvolatile memory (non-transient storage medium) such as ROM (Read Only Memory), flash memory, and HDD (Hard Disk Drive).

The acquisition unit 601 acquires the resistance value (electrical resistance value) detected by the resistance detecting unit 210. The resistance detecting unit 210, for example, detects a resistance value at predetermined time intervals (e.g., every minute). The acquisition unit 601 acquires the resistance value from the resistance detecting unit 210 at predetermined time intervals.

The abnormality determining unit 602 determines whether there is an abnormality in the speed reducer 10 based on the number of times the resistance value acquired by the acquisition unit 601 falls below the threshold value. Specifically, the abnormality determining unit 602 determines an abnormality of the speed reducer 10 when the number of times the resistance value acquired by the acquisition unit 601 falls below the threshold value (second threshold value) reaches the prescribed number of times (e.g., three times). Hereafter, the number of times the resistance value acquired by the acquisition unit 601 falls below the threshold value is referred to as "count". The abnormality determining unit 602 determines that the speed reducer 10 normally operates when the count has not reached a reference count. The storage 610 stores the count.

The output unit 603 outputs the results determined by the abnormality determining unit 602. The output unit 603 transmits the information (the result determined by the abnormality determining unit 602) to an external device. The external device is, for example, a user terminal 300. The user terminal 300 is a computer device located in a facility such as a factory where the speed reducer 10 is used. The computer device is, for example, a desktop PC or a notebook PC, but may also be a tablet terminal or a smartphone. The user terminal 300 displays the results determined by the abnormality determining unit 602 on a display. Specifically, the user terminal 300 displays whether the speed reducer 10 operates normally or not. The output mode of the user terminal 300 is not limited to displaying, but also includes an output mode by sound and storing in a storage medium.

The conductive particle detecting device 100 may be equipped with a light-emitting part such as an LED. In this case, the output unit 603 may make the light-emitting part emit light in a manner according to the determination result made by the abnormality determining unit 602. The output unit 603 may cause the storage 610 to store the determination result by the abnormality determining unit 602.

<Acquisition of Multiple Resistance Values>

In this embodiment, the acquisition unit 601 acquires resistance values between two or more pairs of electrodes in different combinations. Specifically, the acquisition unit 601 acquires the resistance value of channel 1 (the resistance value between the first electrode 130*a* and the second electrode 130*b*) and the resistance value of channel 2 (the resistance value between the first electrode 130*a* and the second electrode 130*c*). Alternatively, the acquisition unit 601 may acquire only one of the resistance values of channel 1 or channel 2. In other words, the conductive particle detecting device 100 only needs to have at least one channel. More specifically, the control device 140 only needs to have at least one of the circuit connecting the first electrode 130*a* and the second electrode 130*b* or the circuit connecting the first electrode 130*a* and the second electrode 130*c* shown in the detecting circuit 200 (see FIG. 4).

In this embodiment, the number of channels is two, but it may be three or more. For example, if the number of the channels is four, a circuit similar to the detecting circuit 200 (see FIG. 4) is provided on the first electrode 130*d* side. Specifically, a circuit connecting the first electrode 130*d* and the second electrode 130*b* via the power supply 201 and a circuit connecting the first electrode 130*d* and the second electrode 130*c* via the power supply 201 may be added. In this way, by providing multiple channels, the long-use metal powder can be detected with greater accuracy.

The abnormality determining unit 602 determines an abnormality based on the count in the multiple channels. Specifically, the abnormality determining unit 602 determines that an abnormality has occurred when the sum of the count in channel 1 and the count in channel 2 reaches the reference count. However, the counts in channel 1 and channel 2 may be measured separately, and when one of the counts reaches the reference count or when each of the counts reaches the reference count, it may be determined that there is an abnormality in the device.

<Informing of Warning and Failure>

In the embodiment, an "abnormality" includes a warning state indicating that the speed reducer is just before a failure and a failure state indicating that it has failed. The abnormality determining unit 602 determines abnormalities including the warning state and the failure state. For example, the abnormality determining unit 602 determines that the speed reducer is in the warning state when the resistance value of one of channels 1 and 2 acquired by the acquisition unit 601 falls below the threshold value (second threshold value) three times. In other words, the abnormality determining unit 602 determines that the speed reducer is in the warning state when the count reaches the reference count (three times). Whereas the abnormality determining unit 602 determines that the speed reducer is in the failure state when the resistance values of both channels 1 and 2 acquired by the acquisition unit 601 fall below the threshold value (second threshold value) simultaneously, regardless of the count.

Alternatively, when the count reaches the reference count (three times), the abnormality determining unit 602 may determine that the speed reducer is in the failure state instead of the warning state. However, even in this case, the speed reducer 10 can still be used for a while. Therefore, the user himself/herself is able to decide whether to continue or stop using the speed reducer 10.

In the embodiment, the threshold value used to determine the failure state (second threshold value) is the same as the threshold value used to determine the warning state (second threshold value). However, the threshold value used to determine the failure state may be different from the threshold value used to determine the warning state. For example, the threshold value used to determine the failure state may be lower than the second threshold value.

Determination of the fault condition when multiple channels are not provided, i.e., when a single channel is provided in the detection circuit 200 (see FIG. 4) will be now described. For example, the abnormality determining unit 602 may determine that the speed reducer is in the failure state when the count is greater than the reference count (e.g., four or more times). The threshold value (e.g., the first threshold value) used to determine the failure state may be lower than the threshold value (the second threshold value) used to determine the warning state, and the abnormality determining unit 602 may determine that there is the failure state when the resistance value obtained by the acquisition unit 601 falls below the first threshold value.

The output unit 603 outputs information indicating either the warning state or failure state. When the abnormality determining unit 602 determines that the reducer is in the warning state, the output unit 603 outputs information indicating the warning state (hereinafter referred to as "warning information"). When the user terminal 300 received the warning information, it informs the user that the reducer is in the warning state by displaying a caution image (e.g., yellow) indicating the warning state on its display. When the conductive particle detecting device 100 is equipped with the light-emitting part, the output unit 603 causes the light-emitting part to emit light in a manner (e.g., yellow) indicating the warning state (caution).

When the abnormality determining unit 602 determines that the reducer is in the failure state, the output unit 603 outputs information indicating the failure state (hereinafter referred to as "failure information"). When the user terminal 300 received the failure information, it informs the user that the reducer is in the failure state by displaying an alert image (e.g., red) indicating the failure state on its display. When the conductive particle detecting device 100 is equipped with the light-emitting part, the output unit 603 causes the light-emitting part to emit light in a manner (e.g., red) indicating the failure state (alert).

<Changing Threshold Value Depending on Size of Reducer>

The timing at which the conductive particle detecting device 100 can detect a failure depends on the size of the speed reducer 10. This is because various factors differ depending on the size of the speed reducer 10, such as the size of the oil bath 22, the amount of the lubricant 13, the amount of long-use metal powder in the speed reducer 10, and the distance from the location where the long-use metal powder is generated to the conductive particle detecting device 100. It is not efficient from the standpoint of manufacturing costs, etc., to manufacture each of the conductive particle detecting devices 100 in accordance with these factors.

Therefore, in the embodiment, the resistance threshold value can be changed according to the size of the speed reducer 10 to accommodate the above factors. For example, when the size of the speed reducer 10 is small, the amount of initial metal powder generated is small, and the location of the conductive particle detecting device 100 is close to the location of the long-use metal powder generated, so the resistance value tends to decrease early. Therefore, when the size of the speed reducer 10 is small, the threshold value for the resistance is set lower to reduce the sensitivity of the detection of the long-use metal powder.

On the other hand, when the size of the speed reducer 10 is large, the amount of initial metal powder generated is large, and the location of the conductive particle detecting device 100 is far from the location where the long-use metal powder is generated, so the resistance value will not easily decrease. For this reason, when the size of the speed reducer 10 is large, the threshold value for the resistance is set higher to increase the sensitivity of detection of the long-use metal powder.

<Changing Threshold Value Depending on Viscosity of Lubricant>

The timing at which the conductive particle detecting device 100 can detect a failure depends on the viscosity of the lubricant 13. This is because, as described above, depending on the viscosity of the lubricant 13, the ease of pushing away the lubricant of the non-conductive layer varies when the long-use metal powder adheres to the conductive particle detecting device 100. Therefore, in the embodiment, the threshold value for the resistance value can be changed depending on the viscosity of the lubricant 13.

For example, when the viscosity of the lubricant 13 is high, the resistance value tends to be difficult to decrease because it is difficult for the long-use metal powder to push away the lubricant when it adheres to the conductive particle detecting device 100. Therefore, when the viscosity of the lubricant 13 is high, the threshold value for the resistance is set higher in order to increase the sensitivity of the detection of the long-use metal powder.

Whereas when the viscosity of the lubricant 13 is low, the resistance value tends to decrease because the long-use metal powder can easily push away the lubricant when it adheres to the conductive particle detecting device 100. Therefore, when the viscosity of the lubricant 13 is low, the threshold value for the resistance is set lower in order to reduce the sensitivity of the detection of the long-use metal powder.

<Changing Threshold Value Depending on Insulating Properties of Lubricant>

The timing at which the conductive particle detecting device 100 can detect a failure depends on the insulating properties of the lubricant 13. This is because the detection accuracy of the resistance value varies depending on the insulation properties of the lubricant 13. Therefore, in the embodiment the threshold value for the resistance can be changed depending on the insulating properties of the lubricant 13.

For example, when the lubricant is not so insulative (i.e., the conductivity is high), the resistance value tends to decrease early. Therefore, when the insulation performance of the lubricant 13 is low, the threshold value for the resistance is set lower in order to reduce the sensitivity of the detection of the long-use metal powder.

Whereas when the lubricant 13 is highly insulative (i.e., when the conductivity is low), the resistance value does not decrease easily. Therefore, when the insulation performance of the lubricant 13 is low, the threshold value for the resistance value is set higher to increase the sensitivity of the detection of the long-use metal powder.

<Changing Reference Count>

In the embodiment, the reference count can be changed depending on the size of the speed reducer 10 to accommodate the above factors. For example, when the size of the speed reducer 10 is small, the resistance value tends to decrease early. Thus, the reference count is set larger to reduce the sensitivity of the detection of the long-use metal powder. Whereas when the size of the speed reducer 10 is large, the resistance value does not decrease easily. Thus, the reference count is set smaller to increase the sensitivity of the detection of the long-use metal powder.

Setting of the threshold value and the reference count can be performed by receiving inputs from a manufacturing staff at the time of manufacture of the control device 140. For example, the control device 140 sets the threshold value and the reference count using the result the inputs received from the manufacturing staff as to whether the size of the speed reducer 10 is greater than or equal to a predetermined size. Specifically, the storage 610 stores in advance a table that maps the size of the speed reducer 10 to the threshold value and a table that maps the size of the speed reducer 10 to the reference count. When the control device 140 received the size of the speed reducer 10, it refers to the table in the storage 610 to set the threshold value and the reference count.

In the embodiment, there are two types of the speed reducer 10 in size, large and small. In addition, for the threshold value and the reference count, one of the two types is set, respectively. However, the size of the speed reducer 10 is not limited to two types, but may be three types (large, medium, and small), or even more than two types. The control device 140 may accept the threshold value itself and/or the reference count itself from the manufacturing staff and set the accepted values.

<Process of Setting Threshold and Reference Count>

Figure 7:
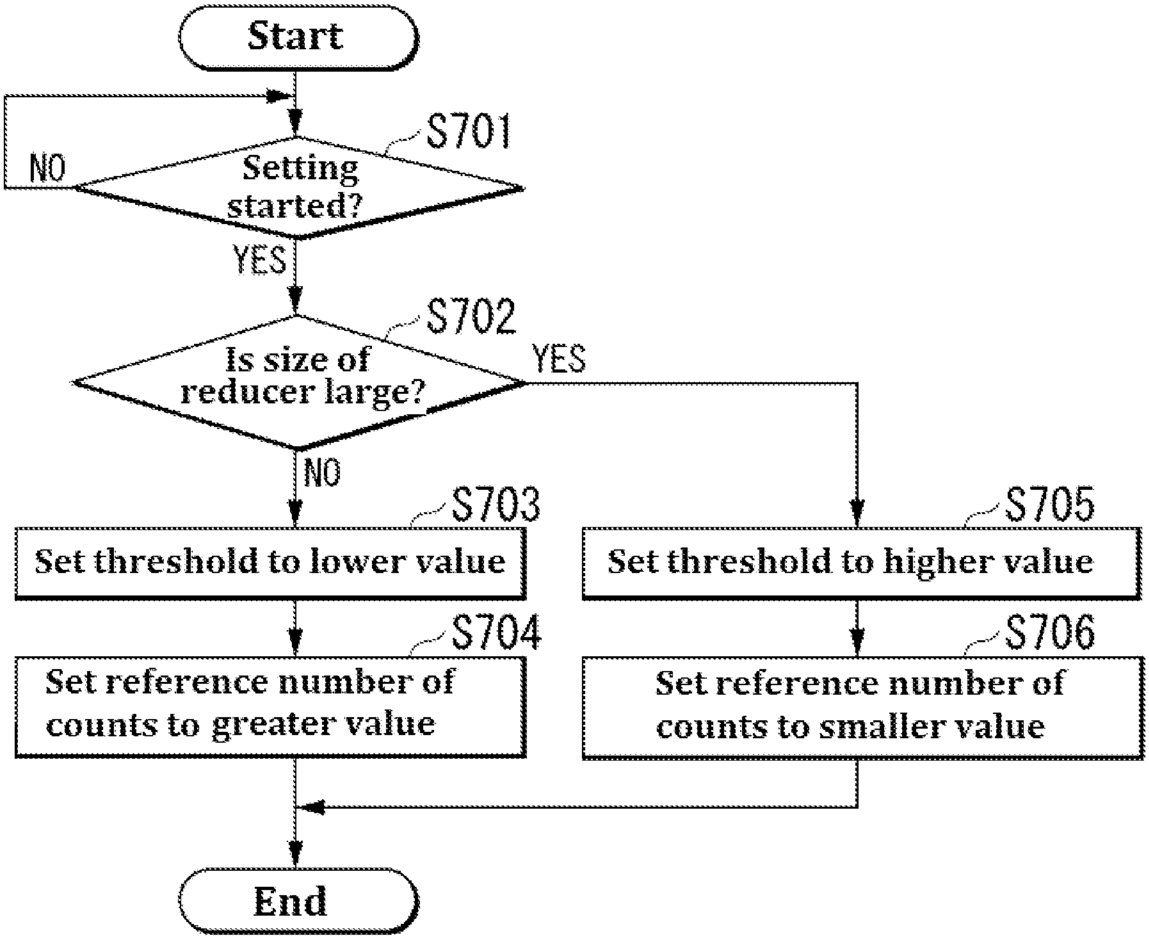
FIG. 7 is a flowchart showing an example of a setting process performed by the control device 140 for a threshold value and reference count.

FIG. 7 is a flowchart showing an example of a setting process performed by the control device 140 for the threshold and reference count. As shown in FIG. 7, the control device 140 waits until it receives a predetermined operation from a manufacturing staff to start setting the threshold value and reference count (step S701: NO). Once the setting of the threshold value and reference count has started (step S701: YES), the control device 140 determines whether the size of the speed reducer 10 received from the manufacturing staff is "large" (step S702).

When the size of the speed reducer 10 is not "large" (step S702: NO), i.e., "small," the control device 140 sets the threshold to a lower value (step S703). Then, the control device 140 sets the reference count to a higher value (step S704) and ends the setting process.

When the size of the speed reducer 10 is "large" (step S702: YES), the control device 140 sets the threshold value to a greater value (step S705). Then, the controller 140 sets the reference count to a smaller value (step S706) and terminates the setting process.

In the flowchart described above, it is also possible to receive at least one of the viscosity and insulating properties of the lubricant 13 from the manufacturing staff and set the threshold according to the received viscosity and insulating properties.

<Abnormality Determination Process>

Figure 8:
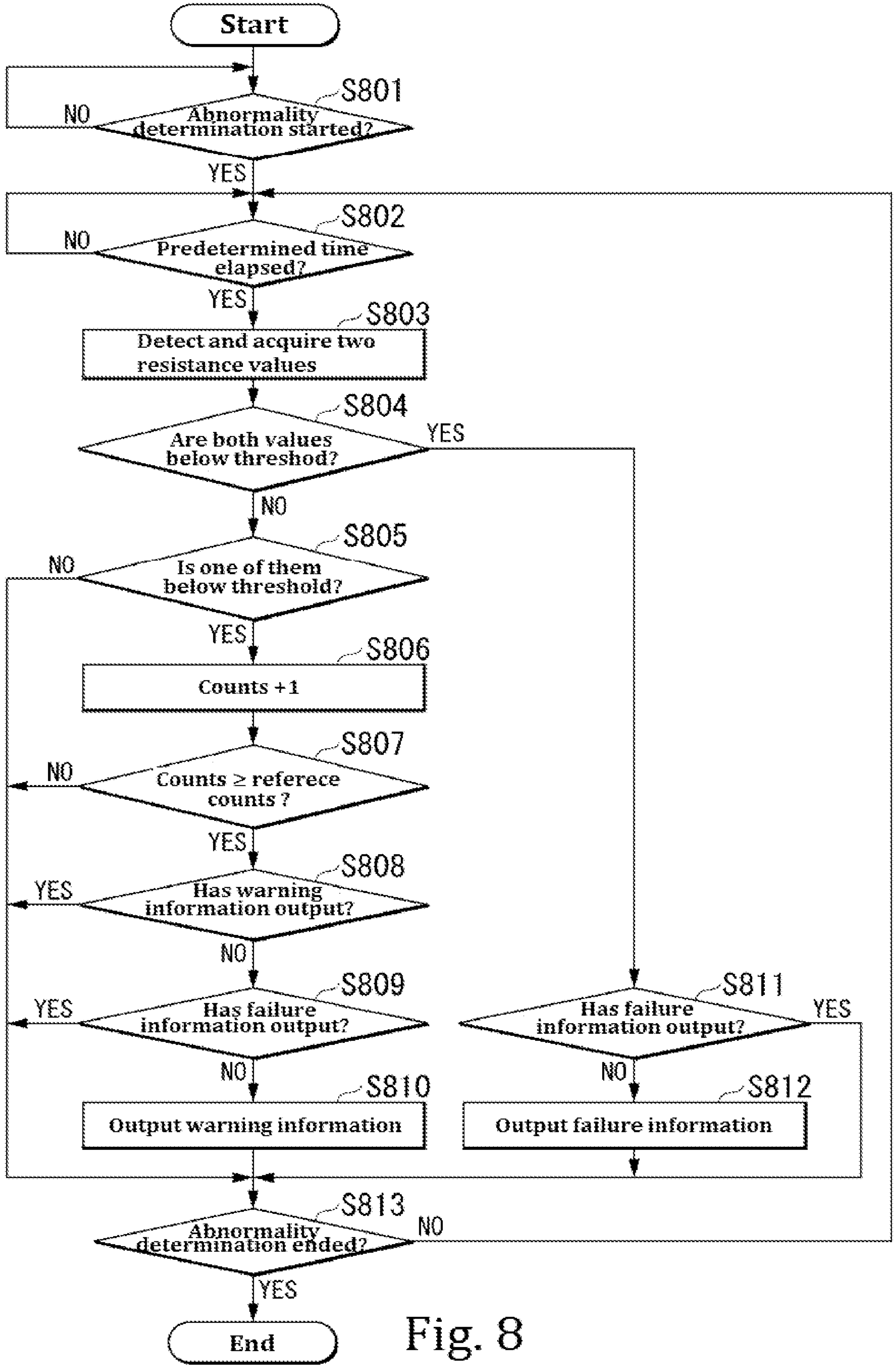
FIG. 8 is a flowchart showing an abnormality determination process performed by the control device 140.

FIG. 8 is a flowchart showing an abnormality determination process performed by the control device 140. As shown in FIG. 8, the control device 140 waits until the start of abnormality determination (step S801: NO). The start of abnormality determination means, for example, that the power of the conductive particle detecting device 100 is turned on. Once the abnormality determination has started (step S801: YES), the control device 140 determines whether a predetermined time (e.g., 1 minute) has elapsed (step S802).

The control device 140 waits until the predetermined time elapses (step S802: NO). When the predetermined time elapses (step S802: YES), the control device 140 detects and acquires values of the two resistances in channels 1 and 2 (step S803). Then, the control device 140 determines whether both of the acquired resistance values are below the threshold (second threshold value) (step S804). When both of the acquired resistance values are not below the threshold (step S804: NO), the control device 140 further determines whether one of the acquired resistance values is below the threshold (second threshold).

When the one of the resistance values is not below the threshold (step S805: NO), i.e., both of the acquired resistance values are above the threshold value, the control device 140 proceeds to step S813. When one of the acquired resistance values is below the threshold (step S805: YES), the control device 140 increments the number of times the resistance value has been below the threshold (count) by one ("+1") and stores the count in the storage 610 (step S806).

The control device 140 then determines whether the count is greater than or equal to the reference count (e.g., three) (step S807). When the count is not greater than or equal to the reference count (step S807: NO), the control device 140 proceeds to step S813. When the count is more than the reference count (step S807: YES), the control device 140 determines whether the warning information has already been outputted to the user terminal 300 (step S808).

When the warning information has already been outputted to the user terminal 300 (step S808: YES), i.e., the user terminal 300 has already been informed of the warning state, the control device 140 proceeds to step S813. Whereas when the warning information has not already been outputted to the user terminal 300 (step S808: NO), the control device 140 determines whether the failure information has already been outputted to the user terminal 300 (step S809).

When the failure information has already been outputted to the user terminal 300 (step S809: YES), i.e., the user terminal 300 has already been informed of the failure state, the control device 140 proceeds to step S813. Whereas when the failure information has not already been outputted to the user terminal 300 (step S809: NO), the control device 140 outputs the warning information to the user terminal 300 (step S810) and proceeds to step S813. The user terminal 300 is informed of the warning state by receiving the warning information.

In the flowchart, when the user terminal 300 has already been informed of the warning state, the warning information is not outputted to the user terminal 300 (step S808:

YES→step S813). However, even if the warning state has been already informed, the warning information may be outputted again to the user terminal 300. The user terminal 300 may inform of the warning state each time it receives the warning information.

When both of the acquired resistance values are below the threshold in step S804 (step S804: YES), the control device 140 determines whether the failure information has already been outputted to the user terminal 300 (step S811). When the failure information has already been outputted to the user terminal 300 (step S811: YES), that is, when the user terminal 300 has already been informed of the failure state, the control device 140 proceeds to step S813. Whereas when the failure information has not already been outputted to the user terminal 300 (step S811: NO), the control device 140 outputs the failure information to the user terminal 300 (step S812). The user terminal 300 is informed of the failure state by receiving the failure information.

In the flowchart, when the user terminal 300 has already been informed of the failure state, the failure information is not outputted to the user terminal 300 (step S811: YES→step S813). However, even if the failure state has already been informed, the failure information may be outputted again to the user terminal 300. The user terminal 300 may inform of the failure status each time it receives the failure information.

The control device 140 then determines whether the abnormality determination is ended (step S813). The end of abnormality determination means, for example, that the power of the conductive particle detecting device 100 is turned off. When the abnormality determination is not ended (step S813: NO), the control device 140 returns to step S802 to continue the detection of the resistance value. Whereas when the abnormality determination is ended (step S813: YES), the control device 140 terminates the process.

As described above, the control device 140 determines an abnormality in the speed reducer 10 based on the number of times the electrical resistance between the electrodes 130 falls below the threshold, and outputs the determination result. This allows the user to be informed of the abnormality that occurs in the preliminary stage of a failure. Thus, the user can use the speed reducer 10 systematically. For example, the user can systematically perform maintenance on the speed reducer 10 during periodic maintenance that is performed by stopping the production line. In addition, the user can avoid the breakdown of the speed reducer 10 during the operation of the production line. Therefore, according to the embodiment, the convenience of users who use the speed reducer 10 can be improved.

The control device 140 of the embodiment determines an abnormality based on the number of times that the multiple resistance values between the different electrodes 130 are below the threshold. This can increase the accuracy pertaining to the abnormality determination because the resistance values can be acquired from the multiple channels.

The control device 140 of the embodiment determines an abnormality based on the sum of the number of times each of the plurality of resistance values falls below the threshold. Thus, it is possible to precociously inform the user of the abnormality that occurs in the preliminary stage of a failure.

The control unit 140 of the embodiment determines an abnormality including a failure state and warning state, and outputs information indicating one of the failure or warning state. This allows the user to be informed whether the speed reducer 10 is in the warning state or failure state. Thus, the user can properly grasp the state of the speed reducer 10.

In the control device 140 of the embodiment, the threshold is a changeable value depending on the size of the reducer 10. This makes it possible to provide the versatile conductive particle detecting device 100 that is compatible with various sizes of the speed reducers 10 simply by changing the threshold value.

In the control device 140 of the embodiment, the threshold is a value that can be changed depending on at least one of the viscosity and insulation properties of the lubricant 13. This makes it possible to provide the versatile conductive particle detecting device 100 that is compatible with various types of the lubricant 13 simply by changing the threshold value.

In the control device 140 of the embodiment, the reference count is a value that can be changed depending on the size of the speed reducer 10. This makes it possible to provide the versatile conductive particle detecting device 100 that is compatible with various sizes of the speed reducers 10 simply by changing the reference count.

The abnormality determination program for realizing the conductive particle detecting device 100 and the control device 140 described above may be stored on a computer-readable storage medium, and the program may be loaded to a computer system to execute the program. The term "computer system" as used herein includes hardware such as an OS and peripheral devices. The "computer-readable storage medium" refers to a storage device such as portable medium including a flexible disc, a magneto-optical disc, a ROM, and a CD-ROM, and a hard disk built-in to the computer system. The "computer-readable storage medium" includes storage that retain the program for some period of time, like a volatile memory (for example, RAM) in a computer system that operates as a server or a client receiving the program through a network such as the Internet or a communication line such as a telephone line. The computer program mentioned above may be transmitted from a computer system that includes a storage device or the like storing the program to another computer system through a transmission medium or by a transmission wave in a transmission medium. The "transmission medium" for transmitting the program refers to a medium that operates to transmit information, like a network (communication network) such as the Internet or a communication line (communication wire) such as the telephone line. Only a part of the functions described above may be implemented in the above program. Further, the functions described above may be implemented by a combination of the above program and other programs previously stored on the computer system. That is, the above program may be what is called a difference file (a difference program).

The foregoing is the description of the embodiments of the present invention with reference to the drawings. Specific configurations are not limited to the above embodiments but include design modifications within the purport of the present invention.

According to the foregoing embodiments and modification examples disclosed herein, a plurality of functions are distributively provided. Some or all of the functions may be integrated. Any one of the functions may be partly or entirely segmented into a plurality of functions, which are distributively provided. Irrespective of whether or not the functions are integrated or distributed, they are acceptable as long as they are configured to attain the object of the invention.

INDUSTRIAL APPLICABILITY

With the above described abnormality determination device, conductive particle detecting device, abnormality determination method, and program, it is possible to improve the user's convenience in using mechanical devices. Accordingly, the present disclosure is industrially applicable.

LIST OF REFERENCE NUMBERS

10 . . . speed reducer (mechanical device), 13 . . . lubricant, 100 . . . conductive particle detecting device, 130 . . . electrode, 131 . . . permanent magnet, 140 . . . control device (abnormality determination device), 210 . . . resistance detecting unit, 601 . . . acquisition unit, 602 . . . abnormality determination unit, 603 . . . output unit, 610 . . . storage

What is claimed is:

1. An abnormality determination device, comprising:

an acquisition unit acquiring an electrical resistance value between electrodes in a non-conductive lubricant used for lubrication of a mechanical device, the electrodes being spaced apart from each other in the lubricant;

an abnormality determining unit determining whether there is an abnormality in the mechanical device based on a number of times the electrical resistance value acquired by the acquisition unit falls below a threshold; and an output unit outputting a result of a determination by the abnormality determining unit, wherein the acquisition unit acquires the electrical resistance value between the electrodes that varies depending on conductive particles collected by magnetic force in the lubricant, wherein the acquisition unit acquires electrical resistance values between two or more pairs of electrodes in different combinations, and wherein the abnormality determining unit determines whether there is an abnormality in the mechanical device based on the number of times the electrical resistance values have fallen below the threshold.

2. The abnormality determination device of claim 1, wherein the abnormality determining unit determines whether there is an abnormality in the mechanical device based on a sum of the number of times each of the electrical resistance values has fallen below the threshold.

3. The abnormality determination device of claim 1, wherein the abnormality determining unit determines a state of the abnormality including a failure state indicating a failure of the mechanical device and a warning state before the failure state, and wherein the output unit outputs information indicating either the failure state or the warning state.

4. The abnormality determination device of claim 1, wherein the threshold is a value that can be changed depending on a size of the mechanical device.

5. The abnormality determination device of claim 1, wherein the threshold is a value that can be changed depending on at least one of viscosity or insulation properties of the lubricant.

6. The abnormality determination device of claim 1, wherein the number of times is a value that can be changed depending on a size of the mechanical device.

7. A conductive particle detecting device, comprising:

electrodes in a non-conductive lubricant used for lubrication of a mechanical device, the electrodes being spaced apart from each other in the lubricant;

an acquisition unit acquiring an electrical resistance value between the electrodes that varies depending on conductive particles collected by magnetic force in the lubricant;

an abnormality determining unit determining whether there is an abnormality in the mechanical device based on a number of times the electrical resistance value acquired by the acquisition unit falls below a threshold; and an output unit outputting a result of a determination by the abnormality determining unit, wherein the acquisition unit acquires electrical resistance values between two or more pairs of electrodes in different combinations, and wherein the abnormality determining unit determines whether there is an abnormality in the mechanical device based on the number of times the electrical resistance values have fallen below the threshold.

8. An abnormality determination method performed by a computer used to control an abnormality determination device, the method comprising:

controlling an acquisition unit of the device to acquire an electrical resistance value between electrodes in a non-conductive lubricant used for lubrication of a mechanical device, the electrodes being spaced apart from each other in the lubricant;

controlling a determination unit of the device to determine whether there is an abnormality in the mechanical device based on a number of times the electrical resistance value acquired by the acquisition unit falls below a threshold; and controlling an output unit of the device to output a result of a determination made by the determination unit, wherein the acquisition unit acquires the electrical resistance value between the electrodes that varies depending on conductive particles collected by magnetic force in the lubricant, wherein the acquisition unit acquires electrical resistance values between two or more pairs of electrodes in different combinations, and wherein the determination unit determines whether there is an abnormality in the mechanical device based on the number of times the electrical resistance values have fallen below the threshold.

* * * * *